United States Patent [19]

Dezes et al.

[11] Patent Number: 5,676,975
[45] Date of Patent: Oct. 14, 1997

[54] BURN SYMPTOM RELIEF COMPOSITION AND METHOD OF PRODUCING SAME

[76] Inventors: Alexander C. Dezes, 104 Sycamore Rd., Severna Park, Md. 21146; George A. Dezes, 1214 S. Charles St., Baltimore, Md. 21230

[21] Appl. No.: 496,432

[22] Filed: Jun. 29, 1995

[51] Int. Cl.$^6$ .......................... A61K 35/54; A61K 35/56; A61K 35/58
[52] U.S. Cl. .................. 424/581; 424/522; 424/195.1; 424/693; 424/688
[58] Field of Search ................................... 424/581, 522, 424/195.1, 693, 688

[56] References Cited

FOREIGN PATENT DOCUMENTS

| | | |
|---|---|---|
| 01038023 | 2/1989 | Japan . |
| 77802 | 10/1984 | Portugal . |
| 1456276 | 11/1976 | United Kingdom . |

Primary Examiner—Jean C. Witz
Attorney, Agent, or Firm—Morton J. Rosenberg; David I. Klein

[57] ABSTRACT

A method of producing a burn symptom relief composition and the burn relief composition is provided which includes the use of blending natural ingredients each to the other to produce the composition for relief of burn symptoms. The method of producing the burn relief composition includes initially separating eggs into egg yolks and egg albumen. The egg yolks are then incorporated into a mixed glyceride composition to form a first intermediate composition which is emulsified by the addition of an aqueous solution of calcium hydroxide. The egg albumen is then mixed with the first intermediate composition to form a second intermediate composition which is further emulsified by the addition of still further additions of aqueous solutions of a calcium hydrate composition which is then stored and applicable for topical application to a mammalian body to relieve the symptoms of pain due to burn conditions.

13 Claims, 1 Drawing Sheet

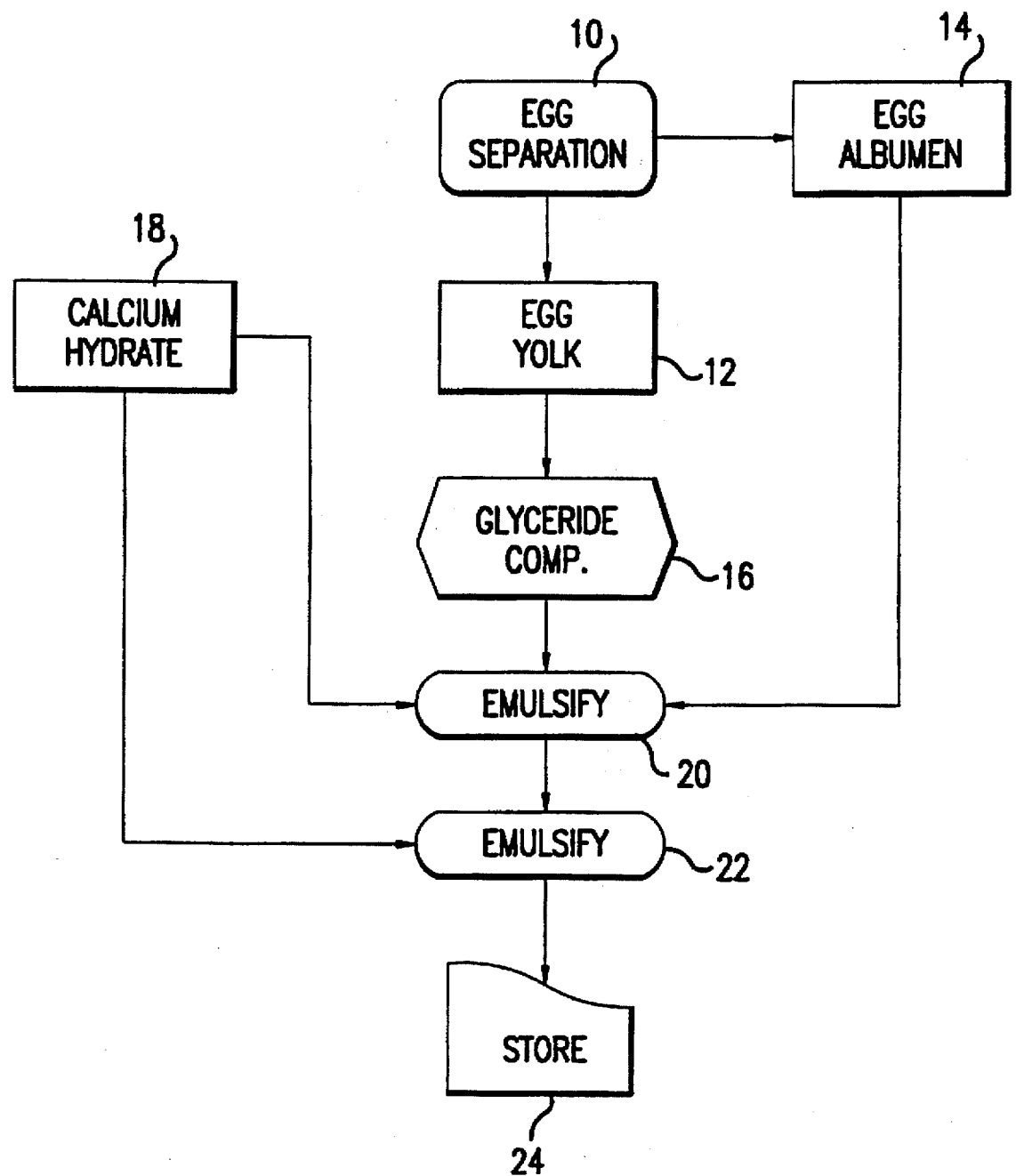

5,676,975

BURN SYMPTOM RELIEF COMPOSITION AND METHOD OF PRODUCING SAME

BACKGROUND OF THE INVENTION

1. Field of the Invention

This invention directs itself to both a method of producing a composition for relieving burn symptoms and further to the burn symptom relief composition as produced by the method incorporated therein. The subject invention pertains to the use of substantially natural ingredients which may be stored and used for topical application to the mammalian body. In particular, the subject invention concept utilizes eggs which are separated into yolk portions and egg albumen portions. Still further, the invention concept directs itself to a method and composition where the egg yolks are incorporated into a mixed glyceride composition which may be a vegetable oil and in particular an olive oil composition forming a first intermediate composition which is then emulsified by the addition of an aqueous calcium hydrate composition. More in particular, this invention directs itself to the addition of the egg albumen to a mixed and emulsified combination of egg yolks and vegetable oil to form a second intermediate composition which is then further emulsified by the addition of an aqueous calcium hydrate composition.

2. Prior Art

Salves or ointments used for topical application to the mammalian body for burns, blisters and other skin surface wounds is well known in the prior art. The best prior art known to Applicant includes U.S. Pat. Nos. 229,014; 1,525,285; 249,069; 451,307; 1,350,842; 1,800,502; 4,219,544; 3,308,020; 5,053,387; 3,548,056; 5,275,806; 3,196,075; 5,047,166; 4,330,527; RE33,993; and, 5,032,394.

Prior art systems such as that shown in U.S. Pat. No. 1,525,285 direct themselves to salves or ointment compositions and include olive oil, egg albumen and salt. In such prior art system bicarbonate of soda has been used however, such does not direct itself to the use of yolk in the combination and incorporation with remaining ingredients as necessary to the subject invention system which is believed to produce an improved burn symptom relief composition.

Other prior art systems such as that shown in U.S. Pat. No. 249,069 are directed to a lotion compound for topical treatment of burns, scalds, sprains and rheumatic pains which includes eggs, oil of cedarwood and table salt. However, such does not provide for the specific ingredients of the subject invention system including the aqueous solution of calcium hydrate in combination with the vegetable oil and further does not direct itself to the separating procedure of the yolks and albumen in production of the overall process.

SUMMARY OF THE INVENTION

A method of producing a composition for relieving burn symptoms which includes the separation of a plurality of eggs into a first egg weight portion consisting of egg yolks and a second egg weight portion consisting of egg albumen. The first egg portion consisting of egg yolks is then incorporated into a predetermined weight of a mixed glyceride composition to form a first intermediate composition. The first intermediate composition is emulsified by incorporation of an aqueous solution of a calcium hydrate composition. The second egg weight portion consisting of the egg albumen is then added to the first intermediate composition to form a second intermediate composition which is then further emulsified by further addition of an aqueous solution of calcium hydrate to form the burn composition of the subject invention.

BRIEF DESCRIPTION OF THE DRAWING

The FIGURE is a schematic block diagram representing the method of producing the subject composition for relieving burn symptoms.

DESCRIPTION OF THE PREFERRED EMBODIMENTS

Referring now to the FIGURE, there is shown a schematic diagram for producing a composition for relieving burn symptoms and the resulting composition. The subject method for producing the burn symptom relieving composition has been found to produce a topically applied composition which relieves burn symptoms such as pain, prevents or substantially reduces blistering caused by sunburn or other burns and is believed to draw heat from the body resulting from sunburn or other burns.

In general, the subject burn symptom relief composition is formed to be topically applied to a mammalian body subsequent to the receipt of burns on the epidermis and has been found to successfully reduce pain, minimize blistering and additionally draw heat from the body.

The burn symptom relief composition as herein described is formed of a plurality of ingredient compositions which are generally naturally occurring and when mixed or blended together appear to have the aforementioned advantages when the mammalian body is subjected to burns.

Referring now to the FIGURE, a plurality of eggs are initially placed in a container with the eggs being separated as shown in block 10 into the constituent parts of the yolk and the albumen or egg whites as depicted in blocks 12 and 14, respectively. The yolks shown in block 12 are mixed or blended in a first container and then incorporated into a mixed glyceride composition in block 16 to form a first intermediate composition.

The mixed glyceride composition is an oil extracted from seeds, fruits or nuts of plants and being plant-derived products are a form of biomass. A number of glyceride compositions may be used including cottonseed, linseed, corn, coconut, babassu, tung, peanut, perilla or olive glycerides.

In the present invention concept, although a number of mixed glyceride compositions have been found to be useful, the vegetable oil formed of olive oil appears to be of excellent quality in mixing with the yolk portion of the eggs and such is easily blendable to produce a first intermediate composition as shown in block 16 of the FIGURE.

Additionally, a calcium hydrate aqueous composition is formed in block 18 which in the preferred composition is calcium hydroxide.

It is surprising that the incorporation and blending of the calcium hydroxide with the remaining ingredients of the subject invention burn relief composition is applicable to topical application to the mammalian body without caustic effects since it has been known in the art that calcium hydroxides may have an irritating effect to the epidermis of the mammalian body.

An aqueous solution of calcium hydroxide is produced as shown in block 18 and then added to the first intermediate composition produced in block 16 for emulsification purposes in block 20. Thus, the egg yolk composition and vegetable oil composition produced in block 16 are emulsified by the addition of the aqueous solution of calcium hydroxide produced in block 18.

Emulsification is provided by a mixing process not important to the inventive concept as herein described with the exception that a generally homogeneous mixture is formed.

After initial emulsification in block 20, the separated egg whites as shown in block 14 are added to a further aqueous solution of calcium hydroxide and are further emulsified in block 22. Once further emulsification is shown by further mixing of a second intermediate composition formed of the egg whites in combination with the first intermediate composition, the burn composition is prepared for bottling or other storage.

Thus, there is provided a method of producing a composition for relieving burn symptoms which includes initially separating a plurality of eggs into a first egg weight portion consisting of egg yolks from block 10 to block 12 and a second egg white proportion consisting of egg albumen shown in block 14.

The first egg portion is then incorporated into a predetermined weight of a mixed glyceride composition shown in block 16 to form the first intermediate composition. The first intermediate composition is emulsified by the addition of an aqueous solution of calcium hydroxide for emulsification purposes as shown in block 20.

The second egg weight portion from block 14 is then added to the first intermediate composition which has been emulsified in block 20 to form a second intermediate composition.

Further emulsification is then provided by further addition of an aqueous solution of calcium hydroxide to the second intermediate composition produced in block 22. Subsequently, the burn preparation is stored in containers or otherwise as is shown in block 24.

The resulting burn symptom relief composition is formed of a plurality of ingredients in predetermined portions which result in a preferred embodiment of the symptom relief composition. Initially, a predetermined weight of egg yolk is added to a mixed glyceride composition which may be a vegetable oil and in particular an olive oil composition. The egg yolk is then mixed with the mixed glyceride composition to form the first intermediate composition. All mixtures are at approximately 1 atmosphere and formed at room temperature approximating 70° F.

A first predetermined weight of calcium hydrate composition is then blended to the first intermediate composition with egg albumen being incorporated or blended with the first intermediate composition to form a second intermediate composition. A second predetermined weight of calcium hydrate composition in the form of an aqueous solution of calcium hydroxide is then added to the second intermediate composition to form the burn symptom relief composition of the subject invention concept.

The basic burn symptom relief composition is formed of an aqueous solution of calcium hydroxide, egg yolks, vegetable oil and egg whites. A preferred approximate batch composition includes initially blending approximately 0.40 ounces of calcium hydroxide with one gallon of water. The first intermediate composition is formed of egg yolks and glyceride with the egg yolks providing approximately 8.0 ounces and the vegetable oil or glyceride being 16 ounces. An initial quantity of egg albumen or egg whites is mixed with the first intermediate composition with the egg whites approximating 16.0 ounces. The calcium hydroxide solution approximating 24 ounces is emulsified and combined with the first intermediate composition and the egg whites to form a second intermediate composition. Finally, approximately 24 ounces of calcium hydroxide solution is then added to the second intermediate composition formed of egg yolks, glyceride, egg albumen and the initial calcium hydroxide solution. The second calcium hydroxide solution approximates 24 ounces. Aloe vera in the amount approximating 1 ounce may be added to the final composition mixture to form the overall burn symptom relief composition.

With regard to the addition of the 0.40 ounces of calcium hydroxide to one gallon of water to form the initial calcium hydroxide composition or solution, it has been found that the preferred range of calcium hydroxide to water is between approximately 0.20–0.60 ounces of calcium hydroxide to one gallon of water. Where the calcium hydroxide is in an amount less than 0.20 ounces, the relief symptom effects appear to be degraded and where the calcium hydroxide is above 0.60 ounces, the relief symptoms appear to be negated.

In the preferred embodiment 8 ounces of egg yolks are mixed with 16 ounces of glyceride composition or vegetable oil and it has been found that a preferred range of the egg yolks to vegetable oil ranges between approximately 4.0 ounces–10.0 ounces per 16 ounces of glyceride or vegetable oil. The preferred range of egg whites is between approximately 12 ounces–20 ounces with respect to the first intermediate composition of 24 ounces formed by the egg yolks and the glyceride composition.

A more homogeneous composition is formed when the initial calcium hydroxide solution in the amount of 24 ounces is initially mixed with the first intermediate composition and then a further calcium hydroxide solution in the amount of approximately 24 ounces is mixed with a second intermediate composition formed of the initial calcium hydroxide solution mixed with the first intermediate composition and the egg albumen. However, acceptable burn symptom relief compositions have been formed with the addition only of a first calcium hydroxide composition to the first intermediate composition and egg albumen mixture. An aloe composition may be blended to the second intermediate composition to provide a pleasing effect.

Additionally, salt may be added to the overall composition and has been found to aid in the burn symptom relief. With relation to the preferred mixture, the quantity of salt added is somewhat minor and may be in the area of 0.5 ounces–1.0 ounces.

Further, sulfite preservatives may be added to the finally derived burn symptom composition prior to insertion into the containers for preservative uses.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended Claims.

What is claimed is:

1. A method of producing a composition for relieving burn symptoms comprising the steps of:
    (a) separating a plurality of eggs into a first egg weight portion consisting of egg yolks and a second egg weight portion consisting of egg albumen;
    (b) combining said first egg weight portion with a mixed glyceride composition to form a first intermediate composition;

(c) emulsifying said first intermediate composition by adding an effective amount of an aqueous composition of calcium hydrate to said first intermediate composition;

(d) adding said second egg weight portion to said first intermediate composition to form a second intermediate composition; and, (e) further emulsifying said second intermediate composition by adding an effective amount of an aqueous composition of calcium hydrate to form a composition for relieving burn symptoms.

2. The method of claim 1 where said calcium hydrate is calcium hydroxide.

3. The method of claim 1 where said mixed glyceride composition is a vegetable oil composition.

4. The method of claim 3 where said vegetable oil composition is olive oil.

5. The method of claim 1 where the first egg portion and the mixed glyceride composition are combined to form a substantially homogeneous first intermediate composition.

6. A burn symptom relief composition produced by the method comprising:

(a) separating a plurality of eggs into a first egg weight portion consisting of egg yolks and a second egg weight portion consisting of egg albumen;

(b) combining said first egg weight portion with a mixed glyceride composition to form a first intermediate composition;

(c) emulsifying said first intermediate composition by adding an effective amount of an aqueous composition of calcium hydrate to said first intermediated composition;

(d) adding said second egg weight portion to said first intermediate composition to form a second intermediate composition; and (e) further emulsifying said second intermediated composition by adding an effective amount of an aqueous composition of calcium hydrate to form a composition for relieving burn symptoms.

7. The burn symptom relief composition of claim 6 where said mixed glyceride composition is a vegetable oil.

8. The burn symptom relief composition of claim 7 where said vegetable oil is olive oil.

9. The burn symptom relief composition of claim 6 where said calcium hydrate composition is calcium hydroxide.

10. The burn symptom relief composition of claim 6 where said first intermediate composition contains a weight percentage ratio of said egg yolk to said mixed glyceride composition of approximately 50%.

11. The burn symptom relief composition of claim 6 where said calcium hydrate is blended to said first intermediate composition in a weight ratio of calcium hydrate to first intermediate composition of approximately 1:1.

12. The burn symptom relief composition of claim 6 where said calcium hydrate composition is added to said second intermediate composition at a weight percentage of approximately 60%.

13. The burn symptom relief composition of claim 6 further comprising an aloe composition blended with said second intermediate composition.

* * * * *